(12) United States Patent
  Portney

(10) Patent No.: US 8,287,593 B2
(45) Date of Patent: Oct. 16, 2012

(54) ADJUSTABLE MULTIFOCAL INTRAOCULAR LENS SYSTEM

(76) Inventor: Valdemar Portney, Newport Coast, CA (US)

( * ) Notice: Subject to any disclaimer, the term of this patent is extended or adjusted under 35 U.S.C. 154(b) by 371 days.

(21) Appl. No.: 12/705,935

(22) Filed: Feb. 15, 2010

(65) Prior Publication Data
  US 2011/0125261 A1    May 26, 2011

Related U.S. Application Data

(60) Provisional application No. 61/264,004, filed on Nov. 24, 2009.

(51) Int. Cl.
  *A61F 2/16* (2006.01)
(52) U.S. Cl. ............. 623/6.32; 623/6.27; 623/6.34
(58) Field of Classification Search ......... 623/6.27, 623/6.32, 6.34
  See application file for complete search history.

(56) References Cited

U.S. PATENT DOCUMENTS

| | | | |
|---|---|---|---|
| 6,197,058 | B1 | 3/2001 | Portney |
| 6,536,899 | B1 | 3/2003 | Fiala |
| 6,991,651 | B2 | 1/2006 | Portney |
| 7,073,906 | B1 | 7/2006 | Portney |
| 2003/0130732 | A1 | 7/2003 | Sarfarazi |
| 2007/0270947 | A1 | 11/2007 | Peyman |
| 2008/0147185 | A1 | 6/2008 | Hong et al. |

*Primary Examiner* — David H Willse
*Assistant Examiner* — Javier Blanco
(74) *Attorney, Agent, or Firm* — Walter A. Hackler

(57) ABSTRACT

An adjustable multifocal intraocular lens system for an individual's eye, includes a base multifocal intraocular lens having an optic with an optical axis, a peripheral edge, a multifocal optical power anterior surface and a posterior surface along with an attachment for maintaining the base multifocal lens in the individual's eye with the optical axis centered along an eye optical axis. An enhanced multifocal intraocular lens is provided with an optic with a peripheral edge, an anterior surface and a reverse multifocal optical power posterior surface, and a coupling enables assembly of the base lens and enhance lens with the enhance lens posterior surface overlaying the base lens anterior surface in order that the enhance intraocular lens reverse multifocal surface adjust multifocal powers of the base IOL by substantially masking near power of the base multifocal intraocular lens.

2 Claims, 6 Drawing Sheets

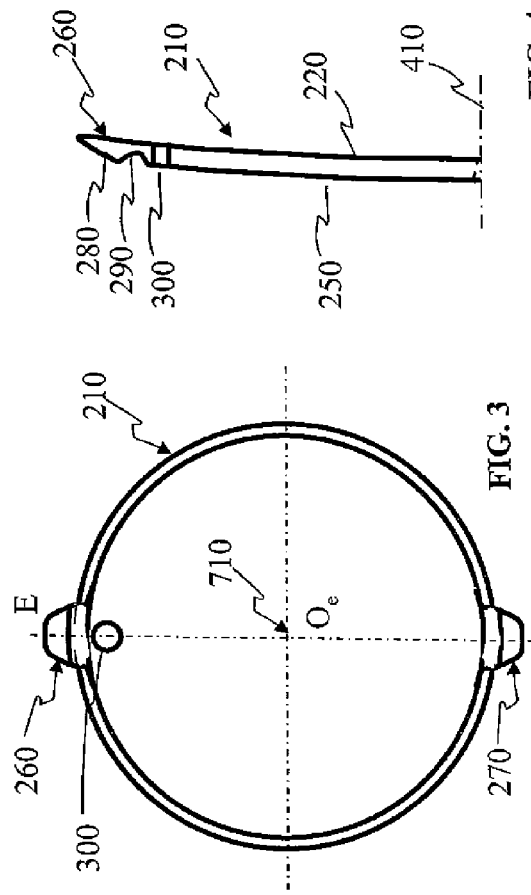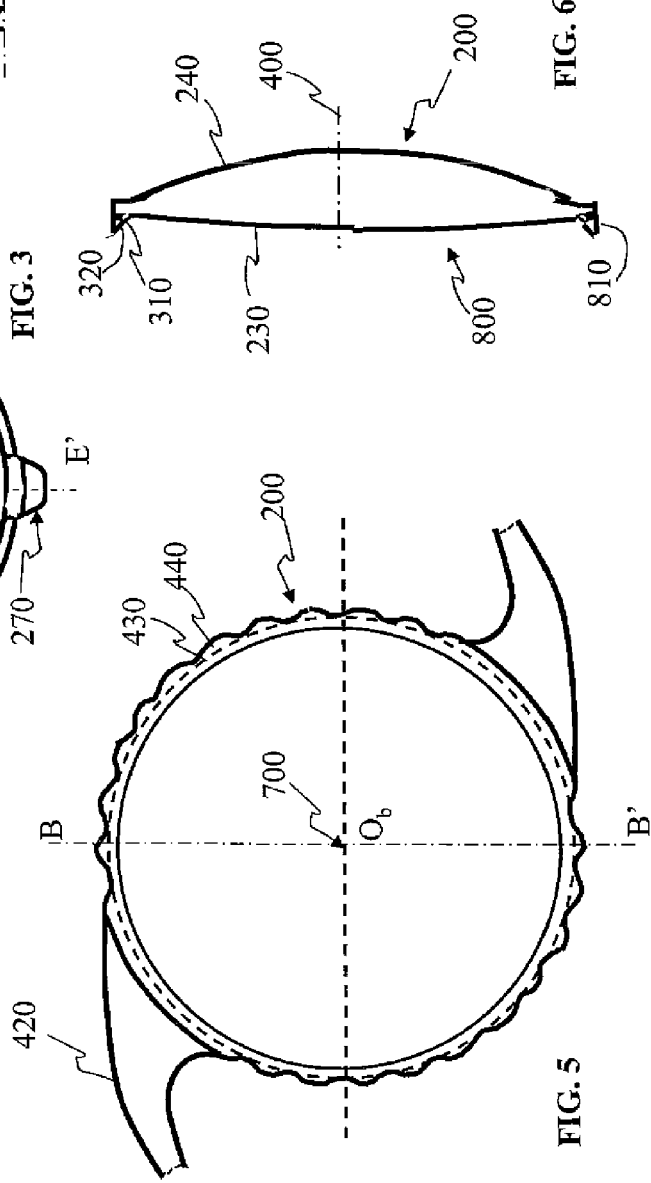

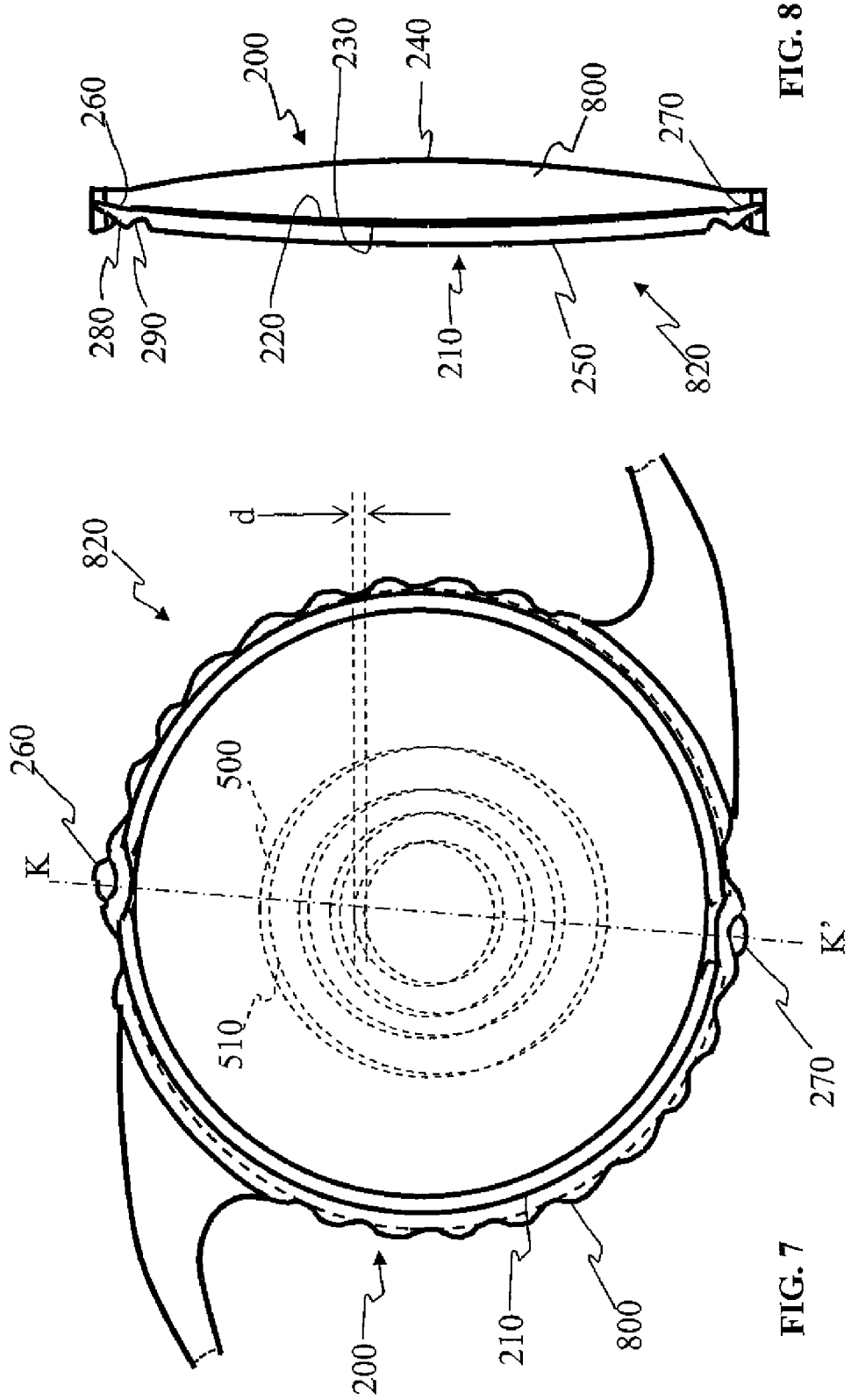

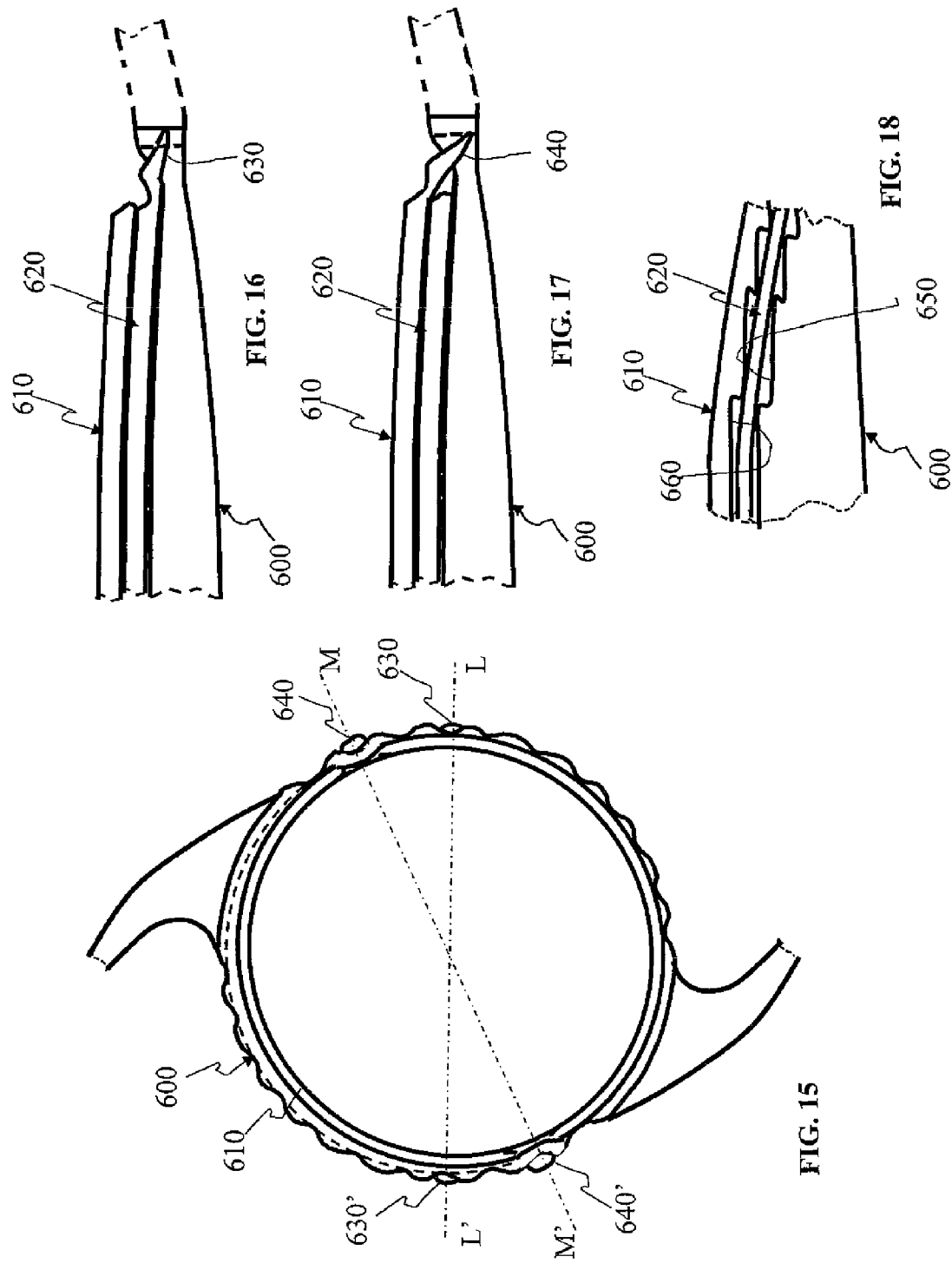

ADJUSTABLE MULTIFOCAL INTRAOCULAR LENS SYSTEM

The present application claims priority from U.S. Ser. No. 61/264,004 filed Nov. 24, 2009. This referenced application is to be incorporated into the present application in its entirety.

FIELD OF THE INVENTION

The present invention relates generally to multifocal intraocular lenses, and more particularly to multifocal intraocular lens of refractive or diffractive powers which is combined with the intraocular lens that mask multifocal lens near power.

BACKGROUND OF THE INVENTION

Two types of multifocal intraocular lenses are known: refraction multifocal IOL (ReZOOM®, for instance) and diffraction multifocal IOL (Tecnis® multifocal, ReSTOR® and OptiVis®, for instance).

Varying power profile of refraction multifocal lens is determined by the wavefront produced by the lens. The power of the lens at a given location or power profile is the local curvature of the wavefront calculated by the second derivative of the wavefront shape with respect to radial position (r) on the lens:

$$Power(r) = \frac{d^2 wavefront(r)}{d^2 r}$$

Power of an ophthalmic optic including multifocal lenses is usually defined by the approximation of the above formula to the axial power calculated by the first derivative of the wavefront shape with respect to radial position (r) on the lens:

$$Power(r) = \frac{1}{r} * \frac{d\, wavefront(r)}{dr}$$

The lens is manufactured by producing front and back surfaces with required surface height profiles $h_f(r)$ and $h_b(r)$. The wavefront produced by the lens is a function of surface heights with respect to radial position (r) on the surface and index of refraction difference at front and back of the lens:

Wavefront$(r) = W_0 + \Delta n_f * h_f(r) + \Delta n_b * h_b(r)$ sub-f and sub-b refer to front and back surfaces Using power profile definition of the wavefront one can calculate Power Profile by the second derivative of the front and back surface height profiles with respect to the radial position (r) on the surface:

$$Power(r) = \Delta n_f \frac{d^2 h_f(r)}{d^2 r} + \Delta n_b \frac{d^2 h_b(r)}{d^2 r}$$

The formula becomes analogues to the Formula for Power of spherical lens, $P = \Delta n \cdot C$, where constant surface curvature (C) is replaced by local curvature C(r) defined by the second derivative of the surface height profile:

$$C_f(r) = \frac{d^2 h_f(r)}{d^2 r} \quad C_b(r) = \frac{d^2 h_b(r)}{d^2 r}$$

Thus, a refraction type multifocal surface is a combination of regions of different surface curvatures.

Diffraction multifocal IOL relies on a different process to produce multiple foci by relying on circular grating zones, also called echelettes or surface-relieve profile or grooves. In a simple paraxial form the surface-relieve profile or blaze shape can be expressed by the formula $r_j^2 = jm\lambda f$, i.e. the focal length of m-order diffraction (m=0, ±1, ±2, etc) for the design wavelength ($\lambda$) can be closely approximated by the following formula:

$$f_m = \frac{r_j^2}{jm\lambda}$$

The formula signifies that a focal length of a given diffraction order is defined by the groove widths. The height of the grooves is responsible for the percentage of light directed to a given diffraction order. In the paraxial approximation the blaze shape height to produce 100% efficiency at m-order is:

$$h_m = \frac{m\lambda}{(n-n')}$$

where n=refractive index of the lens material and n'=refractive index of the surrounding medium.

A diffractive surface may be formed by different shapes of the periodic diffractive structure including one disclosed in U.S. Pat. No. 6,536,899, issued Mar. 25, 2003 and not only by specific blaze shape and for the generality of this invention the term "groove" is used as the description of the variety of shapes of the diffractive structure.

Multifocal IOLs usually provide predictable far and near images for far and near vision in the presbyopia treatment. The problem arises in viewing far bright object at low light condition as the light that passes through the near focus of the multifocal optic creates out of focus image of this far bright object and is perceived by the patient as a halo around the image of the bright source formed by light passing through far focus. The halos are commonly tolerable but in some instances create too much vision disturbance leading to the multifocal lens exchange with a monofocal IOL which eliminates the presence of near focus. The lens exchange is highly traumatic procedure. It is also the procedure that commonly leaves patient with some refractive error because of the uncertainty with power calculation of the exchange monofocal lens and induces surgical changes to the eye due to highly invasive surgical procedure itself.

The phenomenon of halo perception is called multifocal dysphotopsia or photic or entoptic phenomenon. Though the instance of severe multifocal dysphotopsia is fairly small, it is not predictable prior to the surgery which patient may experience it. In short, multifocal dysphotopsia is unpredictable thus creating a significant issue for multifocal IOL use by the surgeons and issue for the patients who may end up with the lens exchange. The present invention addresses the issue of the multifocal dysphotopsia by substantially masking near focus in place of the multifocal lens exchange with monofocal optic. It also addresses another issue of improving image contrast independently to dysphotopsia manifestation as the demand for higher contrast increases with aging if the retinal function deteriorates. The disclosed method of the invention implementation also results in fully predictable visual outcomes for sphero-cylinder error correction and also allows for presbyopia treatment.

SUMMARY OF THE INVENTION

An adjustable multifocal intraocular lens system for an individual's eye comprises a base multifocal intraocular lens having an optic with an optical axis, a peripheral edge, an anterior surface and a posterior surface and a enhance intraocular lens that complement base IOL and thus adjusting the optical characteristics of the base IOL through the combined unit of the base and enhance lenses. The base intraocular lens optic incorporates base multifocal powers, either refraction type or diffraction type or a combination of both. The multifocal power includes near power in addition to far power where near power is defined as an add power to far power that provides near focus at the viewing distance from the eye at about 50 cm and closer.

The multifocal power is placed preferably but not necessary at the front surface of the base IOL. The base intraocular lens incorporates some means to attach enhance IOL to it, for instance, a narrow recess at the lens periphery as described in U.S. Pat. No. 6,197,058 B1 and/or a slit as described in U.S. Pat. No. 6,991,651 formed adjacent the peripheral edge of the base intraocular lens optic. An attachment fixed to the base intraocular lens optic is provided for maintaining the optical axis thereof centered along the optical axis of an individual's eye. The above description of combining enhance and base lenses is preferable embodiment but disclosure is not limited to it and may include other arrangement to practice the disclosed invention.

An enhance intraocular lens having an optic, which preferably has a central thickness between about 0.1 mm and about 0.4 mm, with an anterior surface and a posterior surface, the optic has a reverse multifocal optical power to mask near power of the base multifocal IOL. It may also include, as part of the coupling, for instance, a tab extending generally radially, from the base IOL, as described in U.S. Pat. No. 6,197,058 B1 and U.S. Pat. No. 6,991,651. The attachment tab is sized to penetrate the base intraocular lens recess or slit with the enhance intraocular lens optic posterior surface laying against the base intraocular lens optic multifocal anterior surface, whereby the enhance intraocular lens optic reverse multifocal power provides multifocal power correction of the base intraocular lens multifocal power in order to mask its near power.

In terms of manufacturing by lathing, the base lens can be produced first with the recess and then milled out at the optic periphery portions of the recess into corresponding slits. In case of manufacturing by molding, an appropriate ring is placed to form recess or thin pins are placed to form the slits or a combination of both.

Either enhance IOL or base IOL can be made of the same material or different materials from a group of the foldable materials such as silicone, hydrophilic acrylic, hydrophobic acrylic or other. A surface may be coated to control the adhesive characteristics of enhanced IOL or base IOL.

Adjustable multifocal intraocular system overcomes the issues of ocular trauma of the lens exchange due to multifocal dysphotopsia by placing enhance IOL with reverse multifocal surface that masks near focus over the base multifocal IOL. It also results in precise adjustment for sphero-cylinder refraction error by the base IOL as the required enhance IOL sphere-cylinder power is precisely defined by the patient's refraction and position of the base IOL inside the eye with both parameters can be easily measured. The implantation of enhance IOL involves a minimally invasive procedure because of the volume of the enhance lens is extremely small resulting in the absence of any surgically induced refraction change. Another benefit of the disclosed adjustable system is the improvement in far image contrast as the result of substantially masking near power of the base multifocal IOL by the enhance IOL. The later is important if the patient experiences image quality reduction due to multifocality compounded by an ocular decease and requires improvement of the image contrast. Substantial masking means that the patient can no longer experience near vision.

Thus, the unexpected result of this invention is the ability of enhance intraocular lens to adjust base multifocal refractive or diffractive IOL powers by substantially masking a near power of the base IOL through the combined unit and thus managing multifocal dysphotopsia even with the lenses mutual decentration which may practically occur during surgical procedure.

The additional benefits are a correction for a residual sphere-cylinder refraction error resulted from the base multifocal IOL implantation.

Another additional benefit is improvement in image contrast. A potential problem with multifocal optic may arise many years after cataract surgery due to a reduction in retinal function in conjunction with retinal cells loss, nerve conduction and cerebral cells with macular degeneration and other aging related degradation. The improvement in image contrast may be required independently of the multifocal dysphotopsia.

Another unexpected benefits of the enhance IOL use with base multifocal IOL is the ability to preserve presbyopia treatment even with substantially masking of near power that courses multifocal dysphotopsia by applying monovision or modified monovision.

BRIEF DESCRIPTION OF THE FIGURES

The present invention can be more readily understood by a consideration of the following detailed description when taken in conjunction with the accompanying drawings, in which:

FIG. 3 shows the front view of the enhanced IOL.

FIG. 4 shows a portion of the cross-section of the enhanced IOL.

FIG. 5 shows the front view of the base IOL.

FIG. 6 shows the cross-section of the base IOL optic body.

FIG. 7 shows a front view of the adjustable multifocal intraocular lens system of the present invention with diffraction multifocal power.

FIG. 8 shows the cross-section of the adjustable multifocal intraocular lens system of the present invention with diffraction multifocal power.

FIG. 15 is the front view of the base IOL with two enhance IOLs placed on the top of the base IOL.

FIG. 16 is a portion of cross-section of the adjustable multifocal intraocular lens system of the present invention with diffraction multifocal power of base IOL. The cross-section is taken along the meridian passing through the tabs of the first enhance IOL.

FIG. 17 is a portion of cross-section of the adjustable multifocal intraocular lens system of the present invention with the diffraction multifocal power of base IOL. The cross-section is taken along the meridian passing through the tabs of the second enhance IOL.

FIG. 18 is a portion of cross-section of the adjustable multifocal intraocular lens system of the present invention shown on FIG. 15.

DETAILED DESCRIPTION

Figure 1:
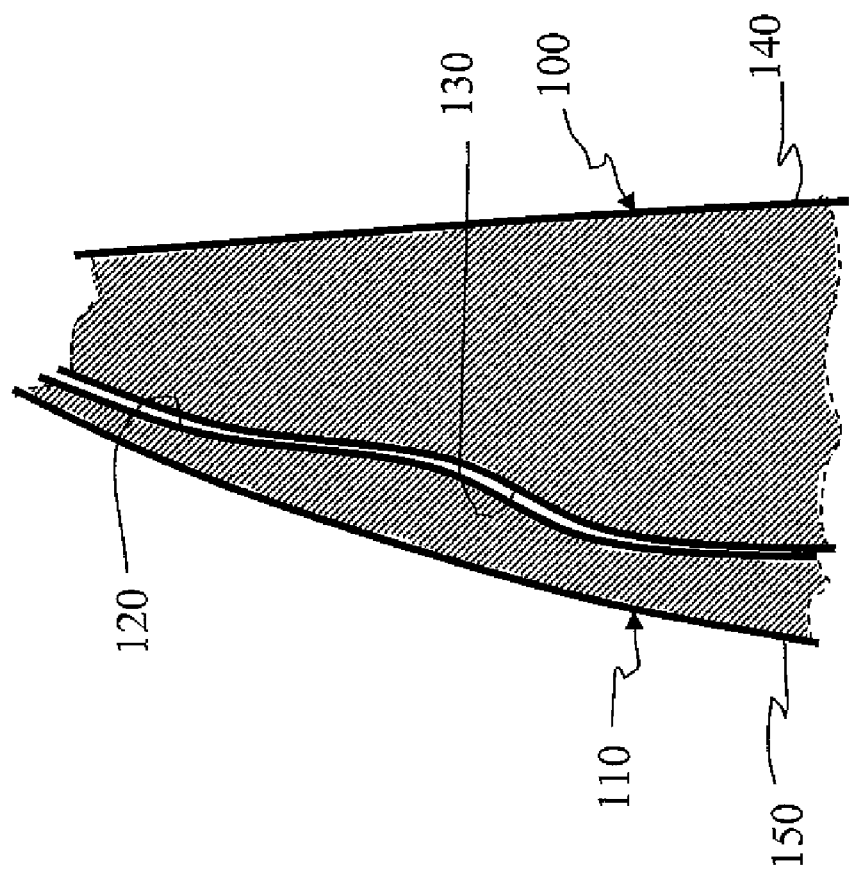
FIG. 1 is a portion of cross-section of the adjustable multifocal intraocular lens system of the present invention with refraction multifocal power and, FIG. 2 is a portion of cross-section of the adjustable multifocal intraocular lens system of the present invention with diffraction multifocal power.

FIG. 1 is a portion of cross-section of the adjustable multifocal intraocular lens system of the present invention with refraction multifocal power. The refraction multifocal surface is a combination of flatter and steeper regions of the surface of different curvatures to produce lower and higher powers for distance, near and/or intermediate vision, i.e. flatter portion is usually corresponds to far power and steeper portion is usually corresponds to intermediate or near power.

Base multifocal refraction IOL 100 is thus configured to provide the multifocal vision correction which is close as possible to the required far vision and also providing the range of vision from far to near, i.e. it includes near power in addition to far power. Since enhance multifocal IOL 110 is configured to provide only a small diopter correction to the base IOL, it may be provided with a spherical power of between about −3.0 and +3.0 diopters and/or; a cylinder power of between about −10.0 and about +10.0 diopters.

The base multifocal IOL 100 incorporates front multifocal refractive surface 130 and back surface 140, which may be spherical or aspheric. Enhance IOL 110 is configured with back reverse multifocal surface 120 to adjust multifocal powers of the base IOL by fully or substantially masking a near power of the multifocal surface 130, i.e. the adjustable multifocal intraocular lens system as the combine unit of 110 and 100 produces primarily far and/or intermediate foci. The enhance and base lenses 110, 100 are shown in contact with each other but in general it is not necessary and reasonably close proximity, in the order of up to about 1.0 can achieve similar outcome so the multifocal surface may be placed on the back of the multifocal base IOL or reverse multifocal surface can be placed on the front of the enhanced IOL. Front surface 150 of the enhance IOL 110 is configured as spherical or aspheric or toric surface or a combination thereof or multifocal surface of up to about 1.5 D Add. The selection of front surface is for a proper adjustment of the base IOL through the combined unit 210 and 200 to achieve desire optical outcomes. Thus, the combined unit may maintain some range of multifocality for modified monovision application if the base multifocal lens includes intermediate power in addition to far power or enhance IOL includes intermediate power in addition to far power. The modified monovision utilizes both eyes where one eye is refracted for far focus and another for intermediate focus. A monovision may be used if the base multifocal lens and enhance IOL do not include intermediate power and the enhance IOL target one eye for far and another eye either for intermediate or near focus though the monovision is less desirable application than modified monovision.

Figure 2:
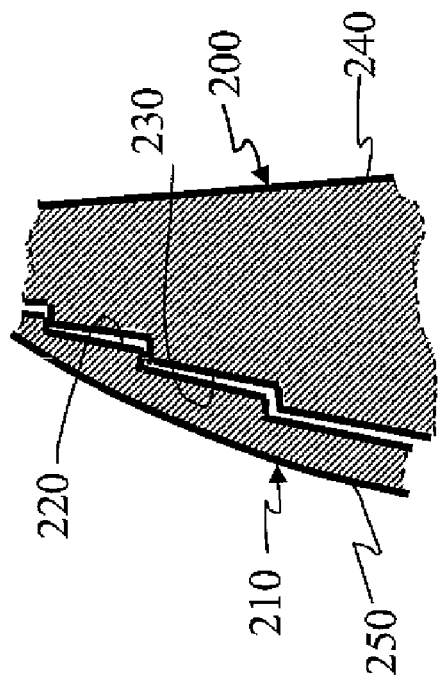

FIG. 2 is a portion of cross-section of the adjustable multifocal intraocular lens system of the present invention with diffraction multifocal power. Base multifocal diffraction IOL 200 is thus configured to provide the multifocal vision correction which is close as possible to the required far vision and also providing near focus or near with intermediate foci. The base multifocal IOL incorporates front multifocal diffractive surface 230 and back surface 240 which may be spherical or aspheric surface. Generally, it is possible to include multifocal surface posteriorly at the base IOL or reverse multifocal surface anteriorly at the enhanced IOL but it is not the best arrangement because it is further away from the reverse multifocal surface of the enhance IOL. Enhance IOL 210 is configured with back reverse multifocal surface 220 to adjust multifocal powers of the base IOL by substantially masking near focus provided by the multifocal surface 230, i.e. the adjustable multifocal intraocular lens system of 210 and 200 produces only far or far and intermediate foci. Front surface 250 of the enhance IOL 210 is usually configured as spherical or aspheric or toric surface for far vision or their combination or multifocal surface of up to about 1.5 D Add. The selection of front surface is for a proper adjustment of the combined unit 210 and 200 to achieve desire optical outcomes. Thus, the combined unit may maintain some range of multifocality for modified monovision application if the base multifocal lens includes intermediate power in addition to far power or enhance IOL includes intermediate power in addition to far power. The modified monovision utilizes both eyes where one eye is refracted for far focus and another eye for intermediate focus. A monovision may be used if the base multifocal lens and enhance IOL do not include intermediate power and the enhance IOL target one eye for far and another eye either for intermediate or near focus though it is less preferable than modified monovision application.

The diffraction multifocal surface 220 is a combination of diffraction grooves with the widths defining the range of powers of the base multifocal IOL 200. The heights of the grooves are responsible for light split between far and near foci. The intermediate powers can included either though a zone of progressive refraction power as described in U.S. Pat. No. 7,073,906 or by including multifocal base surface as described in the US Application Publication No. US-2007/0258143.

With no limitation being intended or implied, base multifocal IOL 100 or 200 is disclosed herein as being a posterior chamber IOL. It is, however, to be understood that base IOL 100 or 200 may alternatively be configured to be implanted in the patient's anterior chamber. It is also to be understood that the base IOL may be a combination of several lenses and for the generality it is still called a "base IOL".

In the preferred embodiment, the base multifocal IOL 100 or 200 incorporates multifocal surface 130 or 230 correspondently at the anterior surface of the base lens. It is, however, to be understood that the multifocal surface may be also placed at the posterior surface 140 or 240 of the base IOL.

FIG. 3 shows the front view of the preferred embodiment of enhanced IOL 210 as described in U.S. Pat. Nos. 6,197,058 and 6,991,651. It is understood that the invention is not limited to the disclosed configuration of the enhance IOL. The enhance IOL 210 includes two tabs 260 and 270 along a meridian EE' through an optic center $O_e$, indicated as 710. The enhance IOL 210 may include at least one hole 300 for easy manipulation by a needle.

FIG. 4 shows a top half of the cross-section of enhanced IOL 210 with front surface 250, back surface 220 and optical axis 410. The tab 260 is shown with particular configuration of a groove 290 and the back of the tab 260 shaped as a continuation of the back surface shape and front shape 280 is slatted to form the wedge. The shape is found to be helpful for its insertion into the slit/recess of the base IOL 200 for the enhance IOL 210 fixation.

FIG. 5 shows the front view of the preferred embodiment of base IOL 200 as described in U.S. Pat. Nos. 6,197,058 and 6,991,651 with recess around an optics body, 420 and slits 430 around the optics body 420 and optical center $O_b$ indicated as 700. There are symmetrical attachments 420 to fixate the optic inside the eye. It is understood that shape of the attachment may be different and is not limited to the particular description. An optical edge 440 of the optic body 420 is shown as wavy being a combination of recesses and slits but it may be conventional circular shape. The benefit of the wavy shape of the optic edge 440 is that a reflection of oblique light off the optic edge becomes diffuse over the wide area at the retina thus reducing a potential for edge dysphotopsia. Another benefit is aroused in clear visible locations of the slits 420 if the enhance IOL tab is configured to penetrate the slit 420. Multiple locations of slits 420 allows precise rotational orientation of the enhance IOL over the base IOL if it includes a toric surface for corneal cylinder correction.

FIG. 6 shows the cross-section of an optic 800 of the base IOL 200 along a meridian BB', see FIG. 5. The optic 800 consists of an optic edge 810, front surface 230 and back surface 240 and peripheral configuration of slatted shape 320 and slit 310. The slatted shape 320 is shaped to maintain centration of the enhanced IOL 210, not shown in FIG. 6, when attaching the enhanced IOL 210 to the base IOL 200 by matching the inside dimension of the slatted shape 320 periphery of the base IOL optic 800 and the optical diameter of the enhanced IOL 210.

FIG. 7 shows a front view of the adjustable multifocal intraocular lens system 820 of the present invention with Base IOL 200 having optic 800 with diffraction multifocal power and enhance IOL 210 placed over it. The tabs 260 and 270 are placed in the slits of the base IOL 200 along the meridian KK'. The lens optics are transparent and the diffractive grooves of the Base IOL 200 and Enhance IOL 210 can be visible as overlapping each other. The enhance IOL 210 diffraction groove widths of the reverse multifocal equal base IOL diffraction groove widths of the corresponding groove number as counted from the lens center, 1, 2, etc. For instance, the $4^{th}$ diffraction groove 500 of the base IOL 200 and $4^{th}$ diffraction groove 510 of the enhance IOL 210 are shown. The Enhance IOL 210 and Base IOL 200 may be not perfectly centered as a practical procedure of the Enhance IOL 210 fixation to the Base IOL 200 and the described two sets of grooves can be seen as mutually decentered which serves as the centration guide to achieve only a small amount of decentration d between the lenses. Groove widths within 3 mm area are in the order of 0.1 mm which allows easily achieve centration of no more than d=0.05 mm as half a groove width magnitude.

FIG. 8 shows the cross-section of the adjustable multifocal intraocular lens system 820 of the present invention along the meridian KK'. It consists of the base multifocal IOL 200 with optic 800 of front diffractive multifocal surface 230 and enhance IOL 210. IOL 200 being in contact with back diffractive reverse multifocal surface 220 of the enhance IOL 210. The tabs 260 and 270 are shown to be placed into slits of the base IOL. Front surface 250 of the enhance IOL can be spherical, aspheric, tonic or even multifocal with the range of power from far to intermediate.

Figure 9:
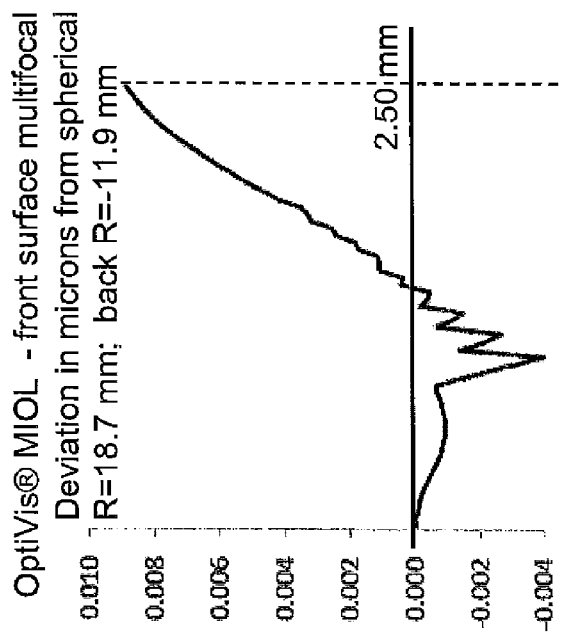
FIG. 9 shows the front multifocal diffractive surface profile of the base multifocal IOL under the model name OptiVis®.

FIG. 9 shows the front multifocal diffractive surface profile of a base IOL of the model name OptiVis® as the deviation from spherical surface of 18.7 mm radius. The deviation in millimeters shown along the vertical axis and distance from the lens center is shown along the horizontal axis also in millimeters. The lens includes the central zone of about 1.5 mm diameter as refractive zone of progressive power to provide intermediate power in addition to far power of the multifocal lens. It includes diffractive zone within 1.5 mm and 3.8 mm diameters to provide far and near foci. The graph shows diffraction grooves of reduced height towards lens periphery, so called apodized diffraction surface. This is to shift larger percent of light towards far focus as the pupil increases and exposes grooves with diminishing heights. The benefits of the combination of central zone of progressive power and diffraction zone for far and near are described in the U.S. Pat. No. 7,073,906.

The diffraction surface also includes aspheric base surface of the diffractive zone and refractive periphery outside 3.8 mm diameter as described in the U.S. application Ser. No. 12/415,742. The aspherization is to produce positive and negative ocular aberrations in far vision at central region and peripheral region of the surface, so called bi-sign aspheric. An aspheric surface is described by the general formula:

$$z(y) = \frac{c \cdot y^2}{1 + \sqrt{(1 - c^2 \cdot y^2)}} + A_4 \cdot y^4 + A_6 \cdot y^6 + A_8 \cdot y^8 + A_{10} \cdot y^{10}$$

Where
  Z-coordinate is along the optical axis
  Y-coordinate is perpendicular to the optical axis
  C is surface curvatures at the vertex defined as reciprocal of the vertex radius $R_v$.

TABLE 1

| Bi-sign aspheric lens parameters. | |
|---|---|
| Parameters | Bi-sign Aspheric (n = 1.494) |
| Front vertex radius $R_v$ (mm) | 17.55 |
| $A_4$ | −0.0015 |
| $A_6$ | 0.000172 |
| $A_8$ | 4.45e−006 |
| $A_{10}$ | −1.1e−006 |
| Back spherical radius R (mm) | −11.90 |

Figure 10:
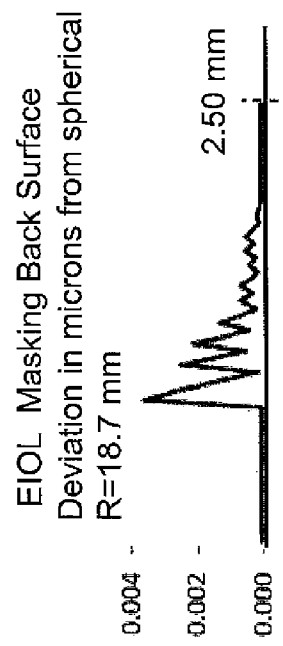
FIG. 10 shows the back reverse multifocal surface profile of the enhance IOL to mask near focus of the OptiVis® base IOL.

FIG. 10 shows the back reverse multifocal surface profile of the enhance IOL placed over the base IOL of the FIG. 9. The surface center within 1.5 mm diameter is spherical surface of radius 18.7 mm, reverse diffractive profile within 1.5 and 3.8 mm diameters shown by the grooves with base surface radius 18.7 mm and peripheral zone outside 3.8 mm is spherical surface of radius 18.7 mm. The grooves are shaped in reverse direction to the diffraction grooved on the FIG. 9. The refractive index of base IOL and enhance IOL were selected the same and equals 1.494. It is understood that the refractive index of the enhance IOL may be different which impacts the diffraction groove heights to compensate the phase shift of the corresponding diffraction groove of the Base IOL.

Figure 11:
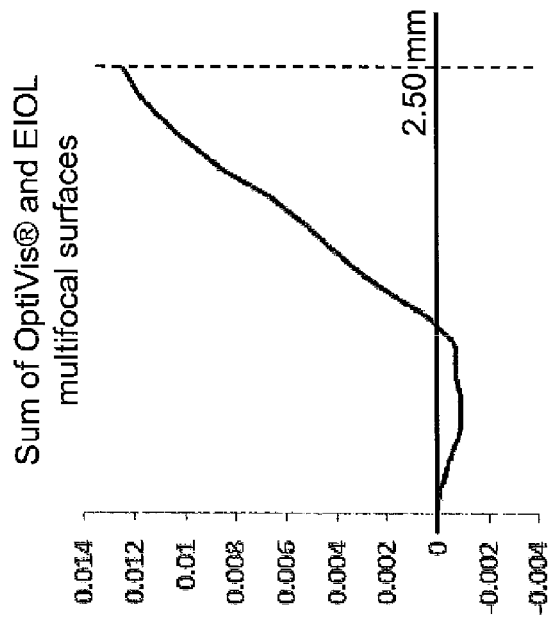
FIG. 11 demonstrates the theoretical profile of sum of the front multifocal diffractive surface profile of OptiVis® base IOL and back reverse multifocal surface profile of the enhance IOL.

FIG. 11 demonstrates the theoretical profile of sum of the front multifocal diffractive surface profile of the base IOL per FIG. 9 and back reverse multifocal surface profile of the enhance IOL per FIG. 10. The result is a removal of the diffraction grooves responsible for the presence of near focus in multifocal diffractive base IOL. All other features of the multifocal base surface such as central progressive power within 1.5 mm and bi-sign asphericity within diffractive and peripheral regions are maintained because Enhance IOL posterior surface is of spherical shape including spherical base surface. This is the reason that combined unit of base and enhance IOLs maintains all features of the base IOL except the absence of near focus produced by the diffraction grooves. As a result, near focus is fully or substantially masked and multifocal dysphotopsia is removed. A patient may not experience severe multifocal dysphotopsia but the image quality in terms of the contrast is reduced due to diminishing retinal function. The image quality is significantly improved with substantial masking near focus. Figures below show the impact of combining Base and Enhance IOLs on the image quality in terms of Modulation Transfer Function (MTF) and Through Focus Response (TFR).

Figure 12A:
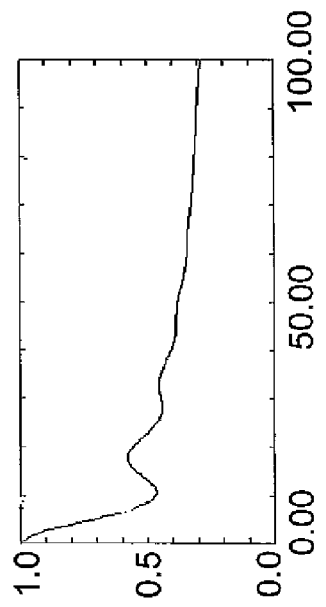
FIG. 12A and FIG. 12B show correspondently Through Focus Response and Far MTF graphs of the OptiVis® multifocal diffractive IOL.
Figure 12B:
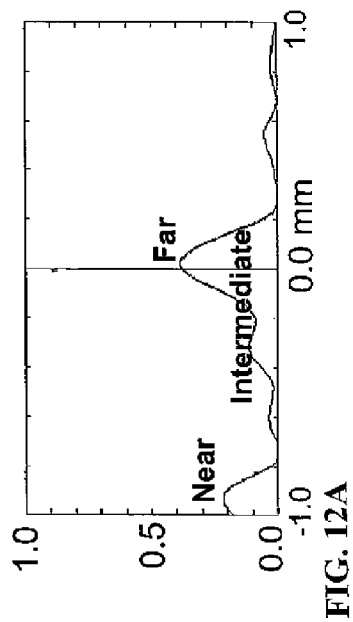

FIG. 12A and FIG. 12B show correspondently Through Focus Response and Far MTF graphs of the OptiVis® multifocal diffractive IOL described in FIG. 9. The TFR includes images at far, intermediate and near distances due to the presence of far, intermediate and near powers. The presence of the Near power creates a potential for halos when viewing far bright object at low light condition as the near image of the object is out of focus.

Figure 13A:
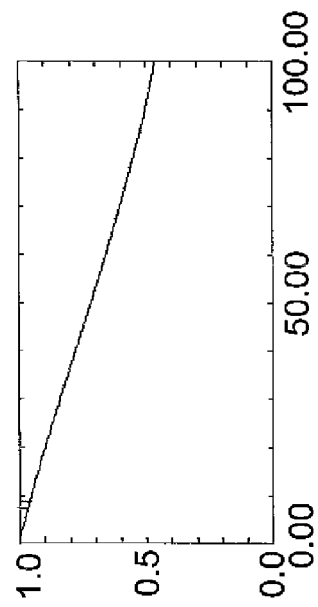
FIG. 13A and FIG. 13B show correspondently Through Focus Response and Far MTF graphs of the adjustable multifocal intraocular lens system with base IOL being the OptiVis® multifocal diffractive IOL and centered enhanced IOL.
Figure 13B:
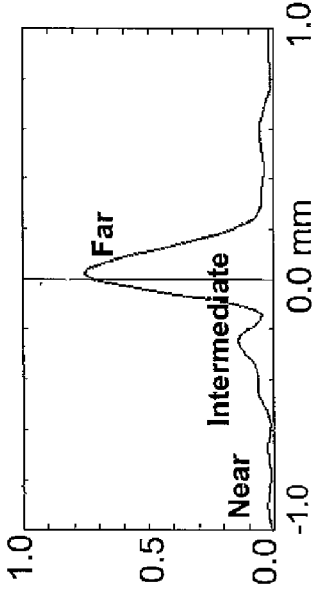

FIG. 13A and FIG. 13B show correspondently Through Focus Response and Far MTF graphs of the adjustable multifocal intraocular lens system with base IOL being OptiVis® multifocal diffractive IOL described by the FIG. 9 and centered enhanced IOL described by the FIG. 10. The TFR shows the absence of near image and presence of far and intermediate images of the combined unit of at least 1 D Add. A reduction in TFR value at near power range below 0.1 unit likely constitutes a substantial masking of Near vision. Absence or substantial removal of Near image confirms the full or substantial masking of near power of the base multifocal IOL. An increase in MTF value by about 0.1 unit or higher at about 50 lp/mm spatial frequency constitutes a substantial MTF improvement. The MTF of the combined unit is substantially increased over the MTF shown on FIG. 12B as a result of substantially masking near power of the multifocal base IOL. A substantial increase in MTF clinically manifested as substantial improvement in image contrast which is important with a patient aging when the retinal imaging function degreases and the enhance IOL with reverse multifocal surface is implanted to improve image contrast independently to a presence of multifocal dysphotopsia.

The existence of the range of power of at least 1 D Add in the combined unit leads to fully predictable modified monovision procedure where one eye is targeted for far and the fellow eye for intermediate together increasing the range of vision to provide near. The targeting far or intermediate at the corresponding eye is fully predictable in case of enhance IOL implantation because the refraction is fully determined by the eye refraction before EIOL implantation and position of the Base IOL from the front corneal surface which is easily measured by A-scan or IOL Master. The result is the preservation of the presbyopia treatment by the procedure of managing multifocal dysphotopsia.

Modified monovision can be achieved even if a combined unit does not manifest intermediate power by including about 1 D Add power into the front surface of the enhance IOL. The Add of around 1 D is not significant enough to produce halos and, as a result modified monovision is fully acceptable.

Figure 14A:
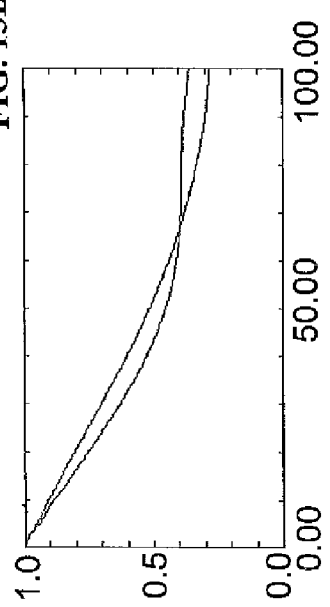
FIG. 14A and FIG. 14B show correspondently Through Focus Response and Far MTF graphs of the adjustable multifocal intraocular lens system with base IOL being the OptiVis® multifocal diffractive IOL and 0.05 mm decentered enhanced IOL.
Figure 14B:
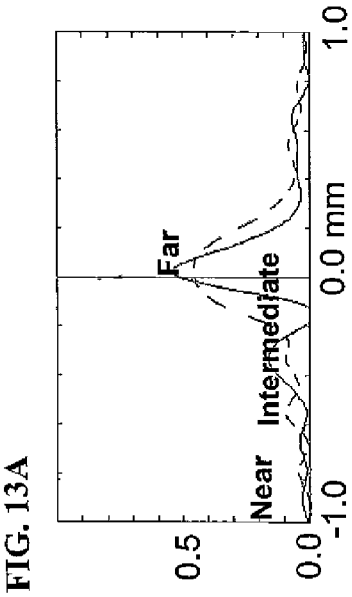

FIG. 14A and FIG. 14B show correspondently Through Focus Response and Far MTF graphs of the adjustable multifocal intraocular lens system with base IOL being OptiVis® multifocal diffractive IOL described by FIG. 9 and decentered by 0.05 mm over it the enhanced IOL described by FIG. 10. The TFR still shows the substantial absence of near image and presence of far and intermediate images of the combined unit. The MTF of the combined unit is still substantially increased over the MTF shown on FIG. 12B as a result of substantially masking near power of the multifocal base IOL and despite of some mutual misalignment between the enhance and base lenses.

FIG. 15 is the front view of a base IOL 600 with two enhance IOLs 610, 620 on the top each other. Bottom enhance IOL 620 has tabs 630 and 630' aligned along the meridian LL'. The top enhance IOL 600 has tabs 640 and 640' aligned along a different meridian MM'. Orientations in different meridians are required to insert the corresponding pair of tabs into different slits of the base IOL 600. The ability to include several enhanced IOLs over the base IOL offers more flexibility to adjust optical characteristics of the base IOL through the combined unit because each enhance IOL can be added at different time in the future as the patient visual condition changes.

There is a benefit to make the base IOL 600 arrangement to enable to place two enhance IOLs 610, 620. About one third of cataract procedures involve eyes with corneal astigmatism of 0.75 D and higher. It is highly desirable to correct corneal astigmatism in order to provide spectacle free vision. As a result, toric enhance IOL 620 is placed together with base multifocal IOL 600 during cataract procedure where one of the surfaces of the tonic enhance IOL 620 incorporates tonic surface with the cylinder magnitude to correct for corneal cylinder. The tonic enhance IOL 620 is easily rotationally aligned over the base IOL 600 for the corneal cylinder correction. The top enhance IOL 610 is implanted if the patient develops severe halos and the top enhance IOL incorporates reverse multifocal surface to mask near power of the base multifocal IOL 600. Again, the top enhance IOL 610 at each eye is selected to provide modified monovision and thus preserving a presbyopia treatment.

In general, the invention does not exclude a condition when the enhance IOL with reverse multifocal surface is implanted first as a result of multifocal dysphotopsia and/or image contrast degradation and the second enhance IOL is implanted to correct for sphero-cylinder.

FIG. 16 is a portion of cross-section of the adjustable multifocal intraocular lens system of the present invention per FIG. 15 along meridian LL'. The enhance IOL 610 is on the top of enhance IOL 620 placed on the top of the base IOL 600. Tab 630 of the enhance IOL 620 is placed in the appropriate slit of the base IOL 600.

FIG. 17 is a portion of cross-section of the adjustable multifocal intraocular lens system of the present invention per FIG. 15 along meridian MM'. The enhance IOL 610 is on the top of enhance IOL 620 placed on the top of the base IOL 600. Tab 640 of the enhance IOL 610 is placed in the appropriate slit of the base IOL 600.

FIG. 18 is a close up of the portion of cross-section of the adjustable multifocal intraocular lens system of the present invention either of FIG. 16 or FIG. 17. The base IOL 600 includes multifocal diffractive surface 650 at its anterior. The bottom enhance IOL 620 shown with smooth both surfaces with either one of them being a tonic surface. Top enhance IOL 610 is shown with reverse multifocal surface 660 at its posterior.

What is claimed is:

1. A method for making an adjustable multifocal intraocular lens (IOL) system for an individual's eye, said method comprising:
   providing a base multifocal intraocular lens having an optic with an optical axis, a peripheral edge, an anterior surface, a posterior surface, and an attachment for maintaining said base multifocal lens in the individual's eye with the optical axis centered along an eye optical axis, with one of the base lens anterior and posterior surfaces having a multifocal optical power;
   providing an enhanced multifocal intraocular lens having an optic with a peripheral edge, an anterior surface, and a posterior surface, with one of the enhanced lens anterior and posterior surfaces having a reverse multifocal optical power;
   providing a coupling enabling assembly of the base lens and enhanced lens; and
   assembling the base lens and enhanced lens with the enhanced lens reverse multifocal optical power surface overlaying the base lens multifocal optical power surface in a manner that the enhanced intraocular lens reverse multifocal optical power surface adjust multifocal powers of the base intraocular lens by substantially masking near power of the multifocal optical power of the base multifocal intraocular lens,
   wherein the reverse multifocal optical power surface of the enhanced multifocal intraocular lens is shaped to substantially match the shape and size of the near region of the multifocal optical power surface of the base multifocal intraocular lens, said multifocal intraocular lens system being multifocal refractive or multifocal diffractive type.

2. The method according to claim 1 wherein the base lens anterior surface is a multifocal optical power surface, the enhanced lens posterior surface has a reverse multifocal optical power and assembling the base lens and enhanced lens includes overlaying the enhanced lens posterior surface onto the base lens anterior surface.

* * * * *